United States Patent [19]
Fletcher et al.

[11] Patent Number: 6,022,353
[45] Date of Patent: *Feb. 8, 2000

[54] SURGICAL SAW BLADE

[75] Inventors: Henry Hasbrouck Fletcher, Cupertino; Michael Gerard Fisher, El Dorado Hills, both of Calif.

[73] Assignee: Synasive Technology, Inc., El Dorado Hills, Calif.

[*] Notice: This patent is subject to a terminal disclaimer.

[21] Appl. No.: 08/153,871

[22] Filed: Nov. 16, 1993

Related U.S. Application Data

[63] Continuation of application No. 07/707,903, May 30, 1991, abandoned.

[51] Int. Cl.⁷ .................................................. A61B 17/00
[52] U.S. Cl. ................................................. 606/79; 606/82
[58] Field of Search ........................ 606/82, 84, 167, 606/176, 177, 178, 180; 83/835, 845, 852

[56] References Cited

U.S. PATENT DOCUMENTS

| | | | |
|---|---|---|---|
| 2,455,655 | 12/1948 | Carroll | 606/178 |
| 2,795,247 | 6/1957 | Topolinski | 83/848 |
| 3,905,105 | 9/1975 | Tuke | 606/176 |
| 3,905,374 | 9/1975 | Winter | 606/178 |
| 4,069,824 | 1/1978 | Weinstock | 606/82 |
| 4,386,609 | 6/1983 | Mongeon | 606/178 |
| 4,513,742 | 4/1985 | Arnegger | 606/178 |
| 4,584,999 | 4/1986 | Arnegger | 606/178 |

*Primary Examiner*—Michael A. Brown
*Attorney, Agent, or Firm*—Daniel J. Meaney, Jr.

[57] ABSTRACT

A cutting saw blade for use with an oscillatory power tool used in surgical bone cutting procedures including a blade having a distal end provided with teeth whose tips are located on a tangent line perpendicular to the long axis of the blade. The teeth are configured substantially as right triangles with their hypotenuses facing either towards the center of the blade or away from the center of the blade. A central tooth can be optionally provided.

12 Claims, 5 Drawing Sheets

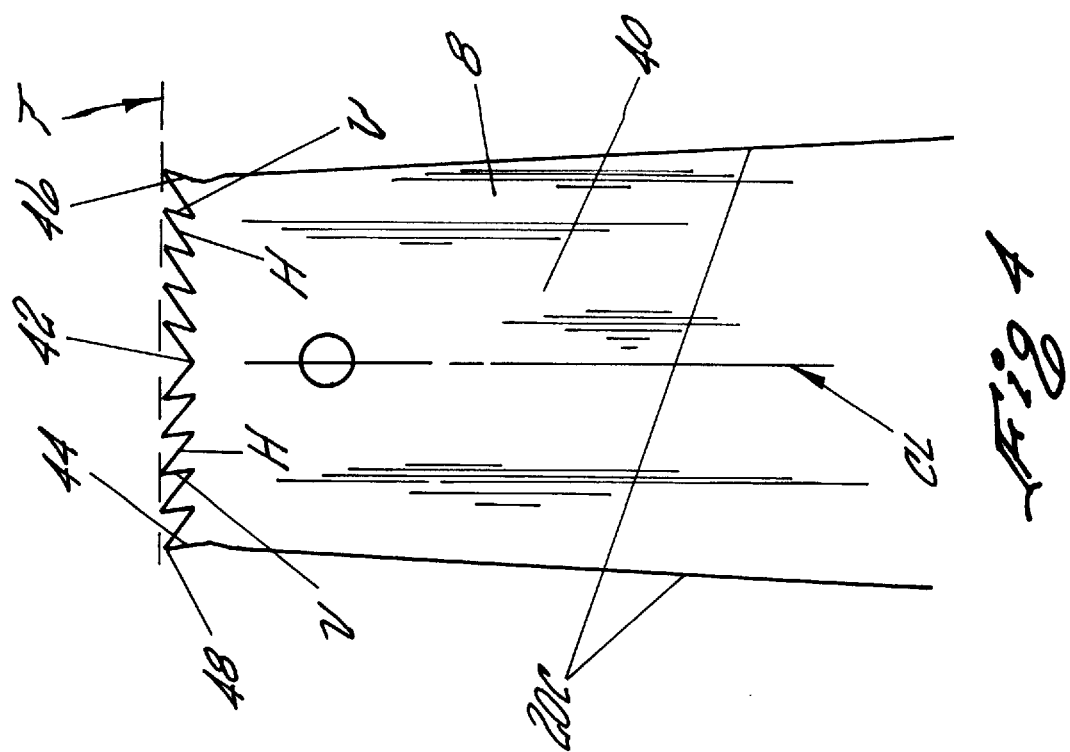
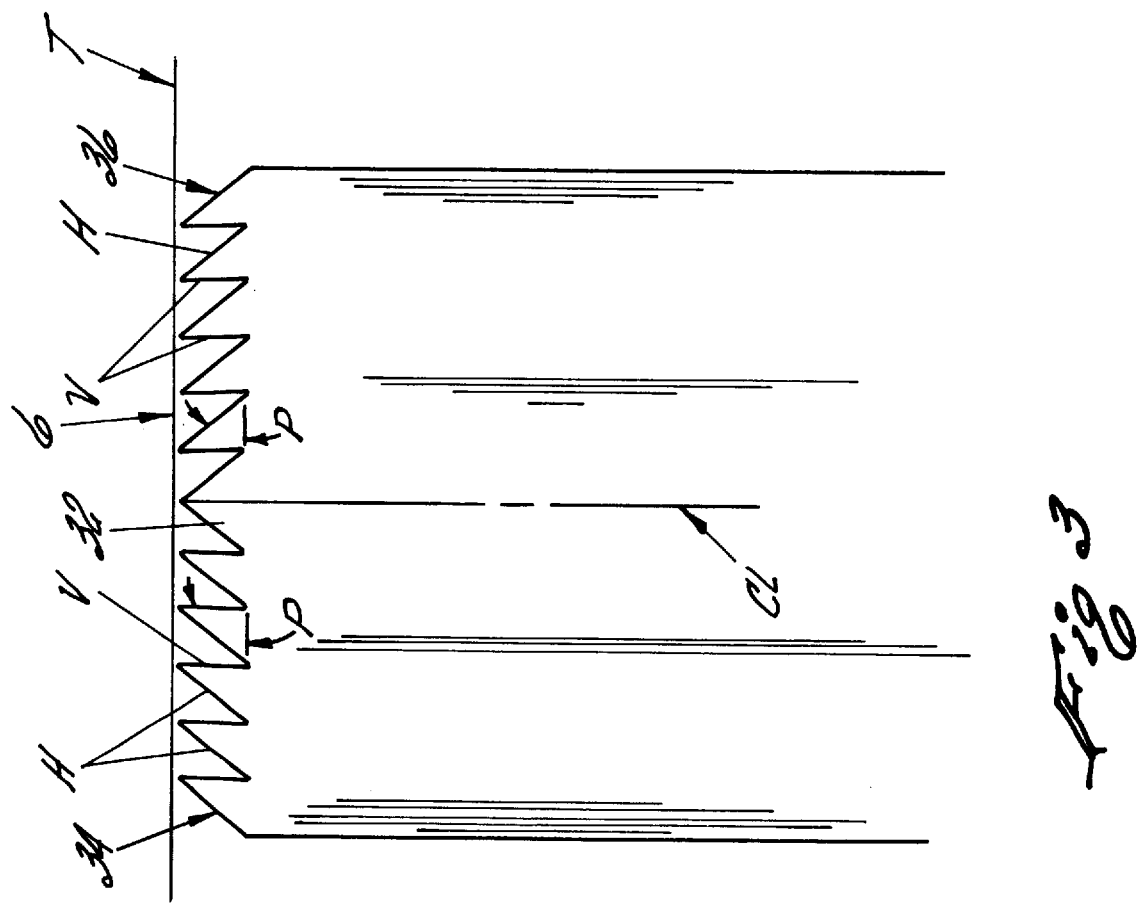

SURGICAL SAW BLADE

This is a continuation of application Ser. No. 07/707,903 filed on May 30, 1991, now abandoned.

FIELD OF THE INVENTION

The following invention relates generally to instrumentalities for cutting bone during surgery. More particularly, the instant invention is directed to a saw blade adapted to be operatively coupled to an oscillatory (or sagittal) surgical power tool which reciprocates the cutting blade back and forth about a small arc.

BACKGROUND OF THE INVENTION

One of the most vexing problems that surgeons face when using surgical bone saws is the tendency of the saw to "kick" i.e., become caught upon the bone being cut by the point of the saw tooth. Another form of kicking occurs where the kerf has the same contour as the blade which is due to the fact that the cutting surface (i.e., teeth) lies on the same radius as the radius of tool rotation. In this scenario, all teeth grab nearly at the same time. This causes the saw apparatus to rotate about that point, transmitting a rotational force back through the saw and to the surgeon. This kicking or grabbing that occurs causes a loss of accuracy in the cut from the sudden, unpredictable movements of the saw and induces increased fatigue of the surgeon because of the greater tension that the surgeon must maintain in his hands and arms in anticipation of receiving this kicking or grabbing motion.

Another problem noted in existing blades involves the tendency of the saw to initially wander rather than to form a kerf. One reason for this involves the nature of oscillatory cutter blades. The handle portion of the saw remains stable because it is in the surgeon's control and remote from the cutting. However a blade (having a proximal end mounted into the oscillatory power tool) moves at a distal end that scribes an arc of a circle. Most surgical cutting saw blades have teeth on the distal extremity which are also oriented in an arc of constant radius. Especially when that arc has a geometrical center which coincides with the center of oscillatory motion, the bone to be penetrated is normally initially addressed by only one active cutting tooth in the series of teeth that resides on the arc, and as the blade completes its outward motion many teeth come into contact simultaneously. With several teeth contacting the bone, there is a greater tendency of the saw blade to kick and wander. The effect is even more pronounced when the blade teeth's center of arc is between the oscillatory center of the power tool and the blade's distal end.

Another problem involves the non-aggressive nature of prior art blades. Even when more than one tooth contacts the bone, it is primarily due to the manipulation of the blade by the surgeon. The effect is that adjacent teeth do not effect progressive cutting and therefore make binding and kick back more likely.

Moreover, once the kerf has formed, several other problems attend the cutting process. For one thing, substantially all the saw's teeth traverse along the entire extent, of the kerf. This decreases the aggressiveness of the cutting action as the cutting action is an abrading one rather than chipping. The teeth reside within the kerf for a longer period of time and tend to naturally generate more heat than had they been allowed outside the kerf. In addition, not having the teeth exit the working surface periodically tends to leave the chips of bone that have been abraded by the teeth to remain between the teeth. Lack of efficient chip removal is recognized as one cause of excessive heat generation. In surgical situations, such unwanted heat generation is undesirable because of thermal necrosis which damages bone structure adjacent to the cut.

The following documents reflect the state of the art of which applicants are aware and are tendered herewith to discharge the applicants' acknowledged duty to disclose relevant prior art of which they are aware. However, it is respectfully stipulated that none of these prior art teachings anticipate when considered singly or render obvious when considered in any conceivable combination the nexus of the instant invention as particularly detailed hereinafter.

| INVENTOR | PATENT NO. | ISSUE DATE |
|---|---|---|
| Carroll | 2,455,655 | 1948 |
| Tuke | 3,905,105 | 1975 |
| Winter | 3,905,374 | 1975 |
| Bent | 3,943,934 | 1976 |
| Mongeon | 4,386,609 | 1983 |
| Arnegger | 4,513,742 | 1985 |
| Arnegger | 4,584,999 | 1986 |

| CATALOG | TITLE |
|---|---|
| Micro-Aire ™ Catalog | "Accessories - Orthopedic Power Instrument System" |
| Stryker ® Surgical Catalog | "Cutting Accessories Guide" |
| Hall Surgical Catalog | "Hall Quality Saw Blades for Stryker and 3M" |

None of the prior art explicitly recognizes the value in having the teeth on an oscillatory cutter placed substantially on a tangent which is perpendicular to a radial line extending from the center of the power tools cutting axis that bisects the arc of travel within which the blade travels.

SUMMARY OF THE INVENTION

The instant invention is distinguished over the known prior art in a multiplicity of ways.

In its essence, the blade of the instant invention takes into consideration the natural tendencies at play when a surgeon is cutting a bone with an oscillatory saw. In general, the natural tendency is to make a plunge type cut, i.e., move the tool and blade in a single direction, plunging the saw in the bone for cutting. The direction of force imposed by the surgeon is intuitively coaxial with the long axis of the saw and blade. When viewed in this light, it should be clear that prior art cutting blades having curved cutting heads will cause the tip of the tooth to either wander or kick. The instant invention, however, addresses the bone to be cut in a manner which reduces fatigue by the surgeon and vibration or impulses generated during the cutting process.

More specifically, when a tooth profile parallels tangents to the arc of travel of the oscillatory cutter, the bone to be cut sees approximately one tooth at a time when the surgeon is making a plunge into the bone. Actually, the contact starts at the center and moves outwards. In this way, there is less pulsed vibration, there is a lower tendency of the saw to kick by having one tooth engage the bone and rotating thereabout, and there is better bone chip evacuation which reduces the operating temperature of the saw adjacent the cut.

One attribute of the instant invention is that each working tooth progressively cuts more material than the previous working tooth so that collectively, all teeth contacting the bone to be cut make progressive contributions.

Three types of saw blades illustrative of these phenomena are disclosed in the instant application. One blade includes a series of cutting tips all oriented in a linear plane and the teeth which support these tips all have the general configuration of isosceles triangles.

A second form of cutting tool is disclosed in which the tips of all of the teeth are also substantially in a horizontal plane, but the teeth which support these tips have a different contour from the first version. A central-most tooth may be in the form of an isosceles triangle as in the first invention form, but the remaining teeth disposed outboard the central isosceles tooth are all substantially right triangles in which the vertical leg of the right triangle is oriented adjacent the central isosceles tooth and the hypotenuse portion is outboard from the central isosceles tooth. This provides a positive rake, and the most aggressive cut as the blade cuts progressively from the inside out.

A third form of cutting blade is shown in which the right triangles of the second version have been oriented 180° so that the hypotenuse of each cutting tooth faces the center of the cutting blade. In practice, the "right" triangles may be "near" right triangles with the included angle greater than 90° for an aggressive cut. The cutting occurs on the tip of the hypotenuse. Also, there is a central isosceles void provided where there had been the central tooth of the second invention form.

OBJECTS OF THE INVENTION

Accordingly, it is the primary object of the present invention to provide a novel and useful cutting saw blade for use in surgery.

A further object of the present invention is to provide a device as characterized above which minimizes the degree of heat buildup associated with the surgical cutting to reduce the thermal necrosis that attends cutting bone.

A further object of the present invention is to provide a device as characterized above which minimizes the backlash and kick that the surgeon experiences when using traditional blades.

A further object of the present invention is to provide a device as characterized above which can be relatively economically manufactured, lends itself to mass production techniques and is extremely durable in construction.

A further object of the present invention is to provide a device as characterized above which cuts aggressively and has a tendency to initially form a kerf, and self centers itself and cuts through the bone quickly within which the blade will reside.

Viewed from one vantage point, it is an object of the present invention to provide a surgical cutting saw blade for penetrating bone when the blade is operatively coupled to an oscillatory power tool. The saw blade has a proximal end and a distal end. The proximal end has means for attachment to the oscillatory power tool for driving engagement thereby. The distal end has a plurality of cutting teeth oriented such that, initially, the outboard teeth contact the bone to be cut to thereby provide better tracking of the saw when forming a kerf in the bone, and the teeth then cut sequentially as the kerf begins to form to provide faster, aggressive cutting and lower temperature cutting through efficient chip removal.

These and other objects will be made manifest when considering the following detailed specification when taken in conjunction with the appended figures.

BRIEF DESCRIPTION OF THE FIGURES

FIG. 3 is a detail of the distal end of the embodiment shown in FIG. 2.

FIG. 4 shows the distal end of a third embodiment.

DESCRIPTION OF PREFERRED EMBODIMENTS

Figure 1:
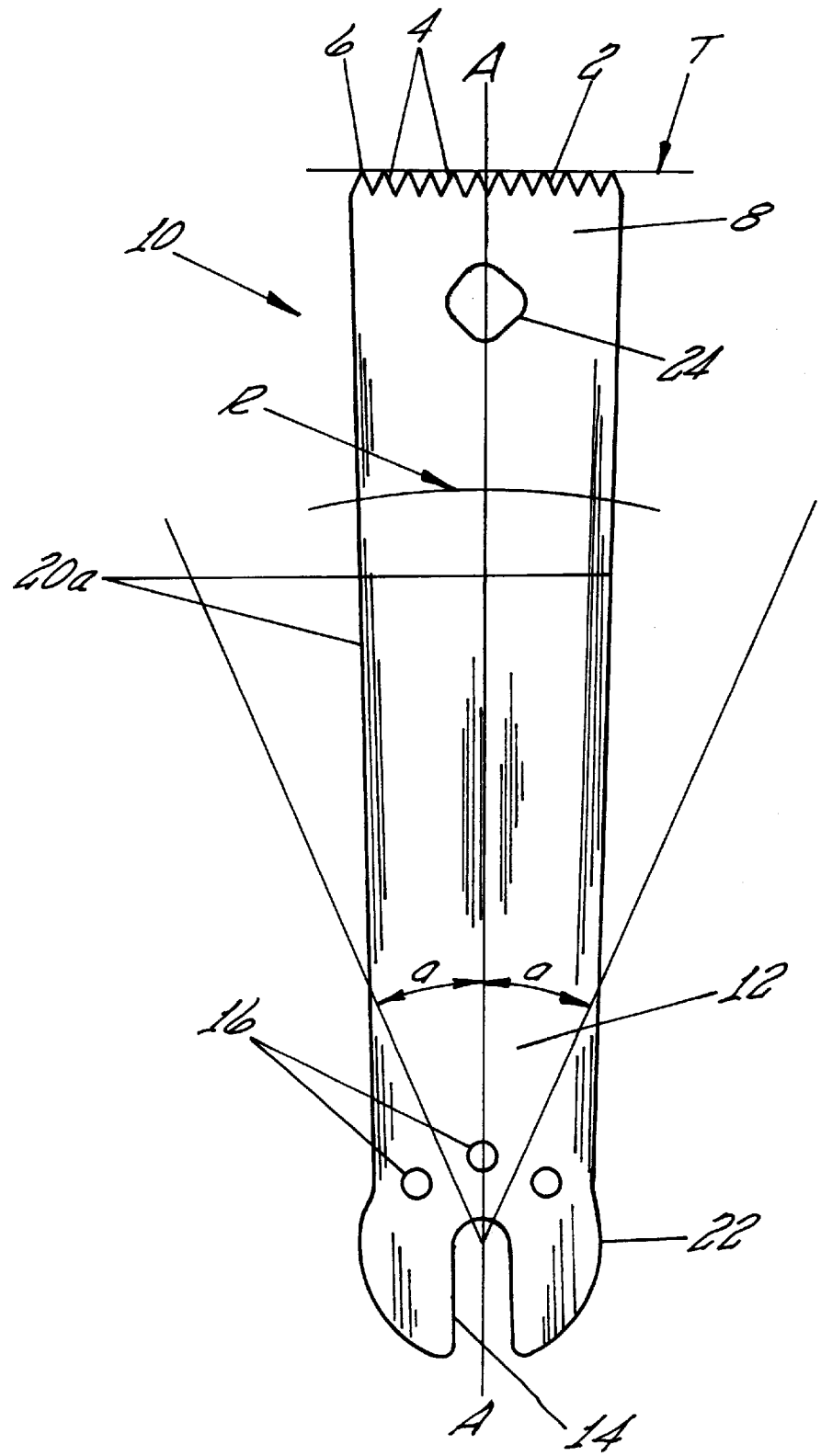
FIG. 1 is a top plan view of the apparatus according to one embodiment of the present invention.

Referring now to the figures, wherein like reference numerals denote to like parts throughout the various figures, reference numeral 10 is directed to the straight saw blade according to one form of the invention, reference numeral 30 is directed to the reverse opposed blade according to the second form of the invention and reference numeral 40 is directed to the outwardly opposed blade according to a third form of the invention.

The straight saw blade 10 of FIG. 1 and according to the present invention includes a distal end 8 upon which a plurality of teeth 2 are positioned and a proximal end 12 which is adapted to coact with and attach to an oscillatory (or sagittal) surgical power tool (not shown).

More specifically, the proximal end 12 has a somewhat bulbous terminus 22 that includes a slot 14 running along the long axis A of the saw blade 10. In addition, a plurality of holes 16 circumscribe portions of the slot adjacent the bulbous terminus 22 to further facilitate interconnection between the saw blade 10 and the oscillatory power tool.

The blade 10 includes a shank 18 interposed between the proximal end 12 and the distal end 8. In general, the shank 18 is formed from substantially flat stock material having side edges 20a which, as shown in FIG. 1, are tapering so that the blade narrows as it goes from the distal end 8 to the proximal end 12.

The distal end 8 of the blade 10 includes, coincident with the long axis A of the blade 10, a diamond shaped cutout 24 having radiused apices at the corners of the diamond. The diamond shaped cutout is oriented such that two of the four radiused apices are coincident with the long axis A of the shank 18. In addition to providing a lighter blade, the diamond shaped orientation tends to assist in tooth profiling during fabrication.

As mentioned, the distal end 8 of the saw blade 10 includes a plurality of teeth 2 disposed on the distal end of the blade 10 remote from the slot 14. Each of the teeth 2 is formed from two sides 4, which coalesce to form the tooth 2. The area of coalescence is defined as tip 6.

As shown in FIG. 1, each of the teeth 2 are formed as isosceles triangles having all tips 6 located on a line T which is tangential to the oscillatory rotation R shown in FIG. 1. Thus, the tips 6 terminate on the tangent line T which is perpendicular to the longitudinal axis A of the cutting blade 10. This is measured when the blade is at an angle which is one-half its maximum arc swing. Typically, an oscillating power tool swings through an arc of 2° to 8° and at speeds ranging from 10,000 cycles per minute to 30,000 cycles per minute.

Figure 2:
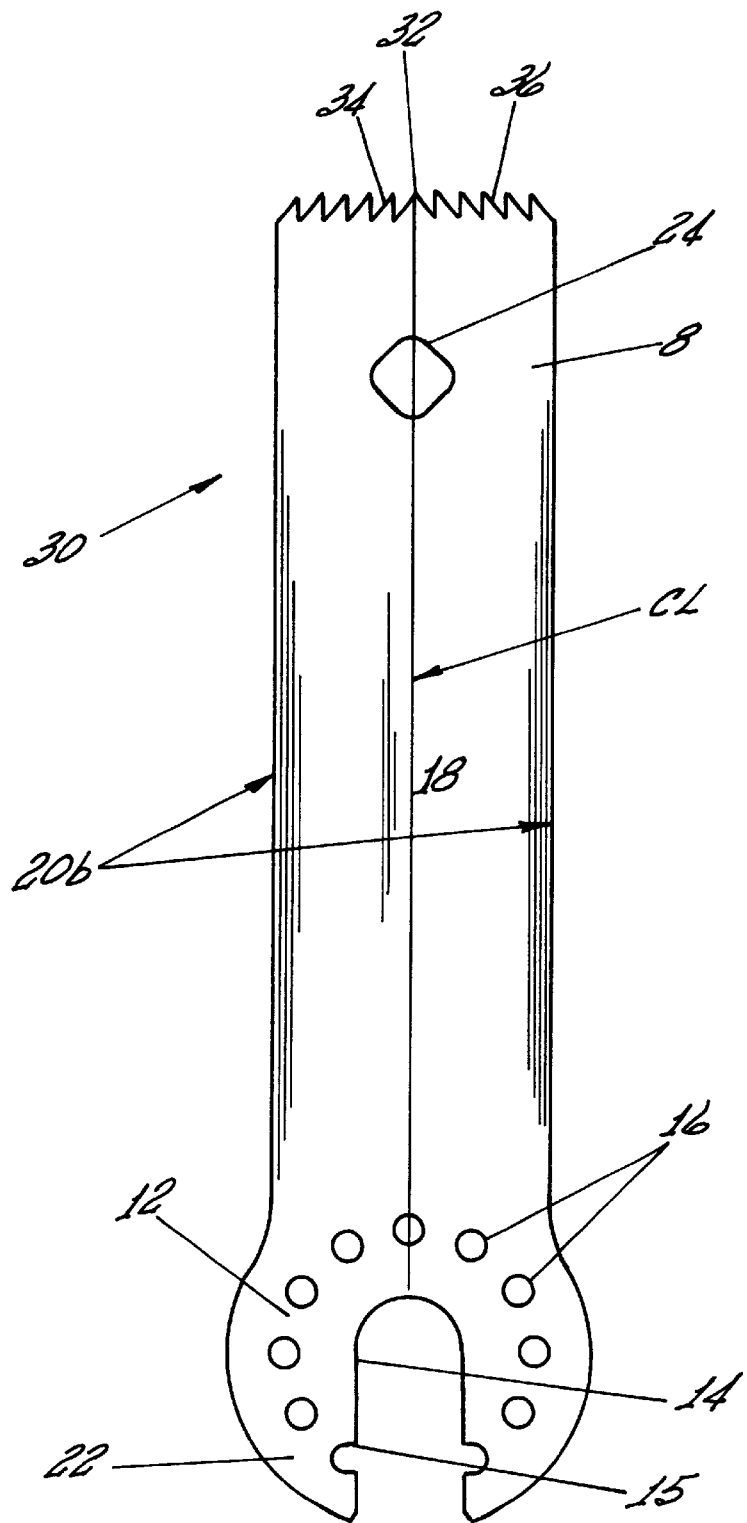
FIG. 2 is a top plan view of a second embodiment similar to FIG. 1.

In a preferred form of the invention, attention is now directed to FIG. 2 which shows a variant of that which is shown in FIG. 1. Tooth details for FIG. 2 are shown in FIG.

3. As shown in FIG. 2, the blade 30 is generally characterized as one which is "reverse opposed" i.e., having a plurality of teeth which are inwardly directed such that when a centerline CL is drawn through the long axis of the blade, two sets of inwardly directed teeth will be evidenced. Those teeth which are to one side of the centerline face those teeth on the other side and are opposed to each other.

The blade 30 also shows that the proximal end 12 includes a bulbous terminus 22 as described with respect to FIG. 1 but in addition to the slot 14 running parallel to the long axis or center line CL, a pair of recesses 15 extend inwardly on linear portions of the U-shaped slot for additional attachment to the oscillatory power tool. Moreover, additional holes 16 circumscribe the U-shaped slot 14 to provide additional retention and drive points when connected to the oscillatory power tool.

The shank 18 is formed from flat stock material whose side edges 20b extend from the distal end 8 to the proximal end 12 but, unlike FIG. 1, these side edges 20b are parallel.

With respect to FIG. 3, certain details of the tooth configuration can also now be best appreciated. As shown, the center line reflects that one central tooth 32 has an apex or tip coincident with the center line CL of the long axis of the blade 30. Thus, the central tooth 32 is depicted as forming a substantially isosceles triangle similar to the teeth 2 shown in FIG. 1. However, the center line CL serves as a line of demarcation between the left lateral side of blade 30 and the right lateral side of blade 30. As shown, the left lateral side includes a plurality of inwardly (i.e. towards central tooth 32) canted teeth 34. Conversely, the right lateral teeth 36 are also inwardly canted toward the central isosceles tooth 32. Both of the left lateral teeth 34 and right lateral teeth 36 are formed substantially as right triangles with the right angle denoted by p. Actually p can be slightly greater than 90° to provide a positive tooth rake when cutting.

Figure 5A:
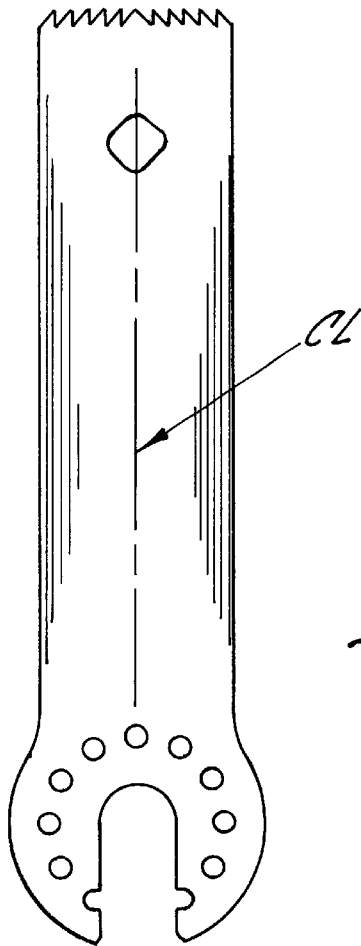
FIG. 5A diagrammatically shows the blade of the present invention posed to begin a cut.
Figure 5B:
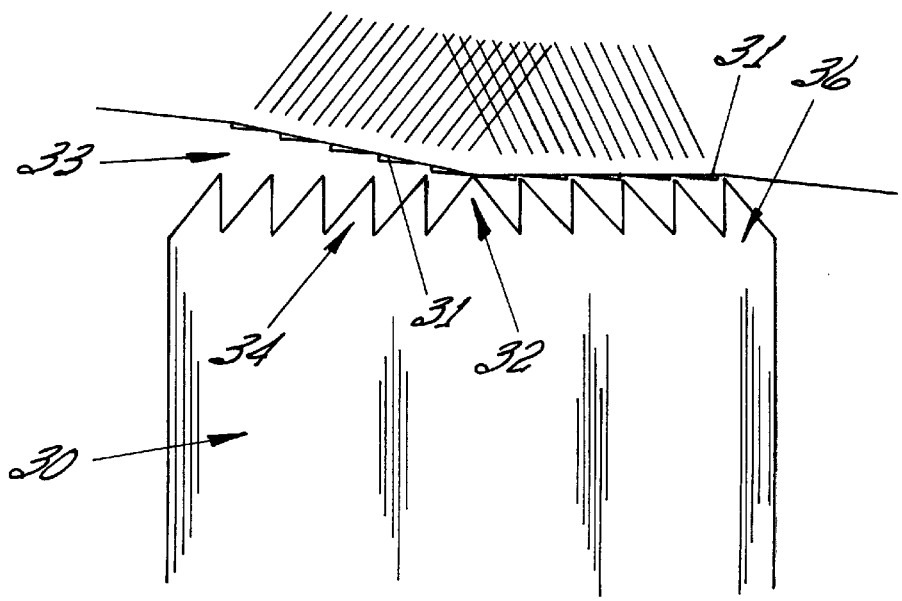
FIG. 5B shows the FIG. 5A blade having progressed partially through a cut.

The hypotenuse leg H of each tooth 34 and 36 is outboard with respect to its vertical leg V. As shown, when p is greater than 90°, leg V slopes towards the center line CL providing a positive rake. In this manner, teeth 34 and 36 on opposite sides of the central tooth 32 "oppose" each other when cutting. In cutting, FIG. 5A shows the blade poised and oriented tangential to the bone and the teeth perpendicular to the center line CL. FIG. 5B shows the cut after progress has been made in the cut. The cut has been exaggerated to explain the effect.

The kerf 33 is actually V shaped about central tooth 32. As the right side teeth 36 cuts (FIG. 5B), the left side teeth 34 are cooling and cleaning. As shown, the last tooth 36 has just finished cutting and the tooth labeled 34 is about to begin a cut. In effect, each tooth progressively takes a small cut 31 on each oscillatory stroke from the center then laterally outwards. This can be viewed as "progressive staircasing" with the stairs 31 being removed one at a time. Stated alternatively, FIG. 5B shows a blade 30 in an advanced stroke of oscillation where the staircase of material on the left side of the center tooth 32 has already been removed (in an earlier stroke). Then the blade goes into this advanced stroke and has just completely finished this stroke where tooth 36 has stopped its leftward or inward motion and this progressive staircase looking kerf has been formed. As can be envisioned, when the left side teeth 34 are working, the right side teeth 36 are cooling and being cleaned of chips. A very slight V shaped kerf is formed in practice.

The active cutting tip 6 is the end of the vertical leg V where it contacts leg H. The central tooth 32 is optional.

Note the teeth in the FIG. 3 embodiment also terminate along a tangent line T which is at right angles to the centerline CL.

With respect to FIG. 4, it is to be observed that the proximal end of the FIG. 4 version has not been shown. This is due to the fact that it could be accommodated by many commercially available or by either the FIG. 1 or the FIG. 2 variants and will not be belabored here. However, the distal end 8 of the FIG. 4 version bears some differences which need to be addressed. This version 40 is distinguished from the first version 10 and second version 30 by including a plurality of outwardly opposed teeth.

More specifically, the center line CL of the FIG. 4 version 40 serves as an line of demarcation between the left side teeth 44 and the right side teeth 46. The center line CL, when bisecting between the left side teeth 44 and the right side teeth 46, passes through a central isosceles void 42 (i.e. the absence of a central tooth). The tooth structure 44 and 46 is similar to the FIG. 2 and 3 structure. However, the hypotenuse leg H of these triangles has been transposed 180° so that this leg now faces the central isosceles void 42 and the vertical leg V is canted slightly to the "outside", i.e. away from the center line CL and center isosceles void 42, providing a negative rake. Using this structure, it is possible to appreciate that the teeth 44 and 46 according to this version work opposite from the teeth 44 and 46 shown in FIGS. 2 and 3. However, all teeth in all versions are substantially "flat-top" configured, i.e., the tips stop at the tangent T perpendicular to the center line CL. Note the tip 48 of the outermost teeth 44 and 46 extend beyond the side edges 20c. The aggressive cutting pattern of the blade 40 shown in FIG. 4 has excellent chip clearing properties analogous to FIG. 5B, but opposite therefrom.

Figure 6A:
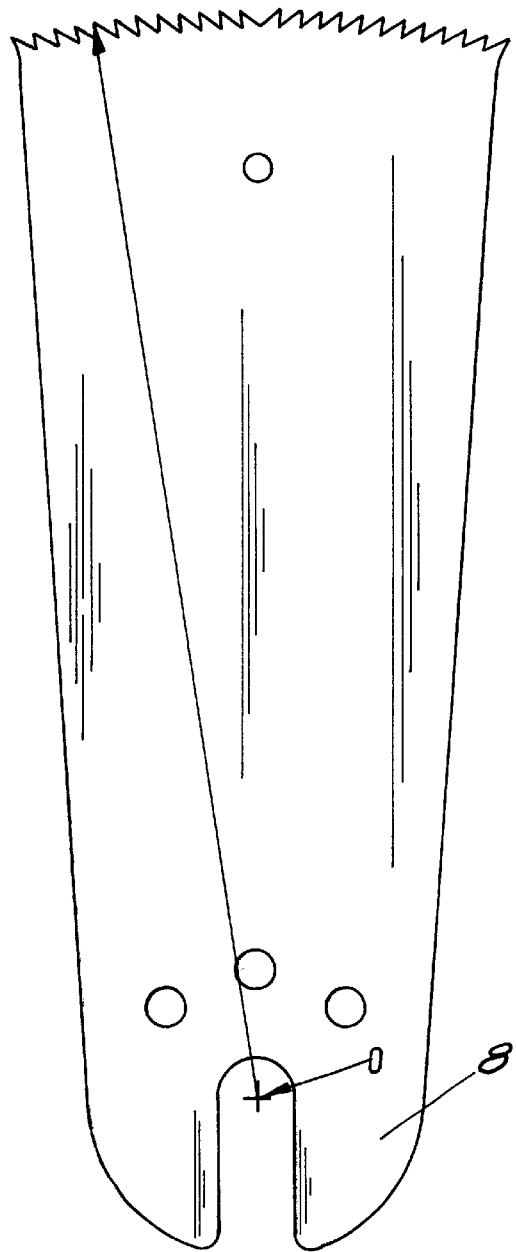
FIGS. 6A and 6B parallel FIGS. 5A and 5B respectively but show prior art.
Figure 6B:
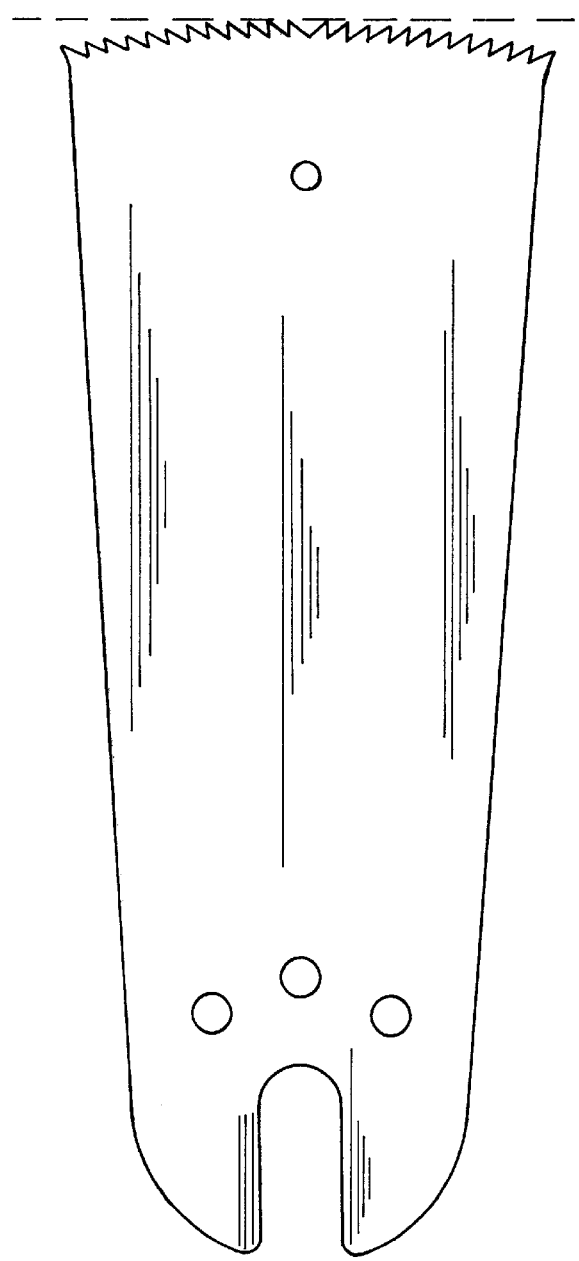

Prior art FIGS. 6A and 6B show the effect of cutting teeth on a curve such that the radius r falls between the oscillatory axis 0 and the distal end 8. In use, only very few teeth actually do the cutting work and the cutting is not progressively advanced. As "r" gets larger—approaching the "flat-top" structure preferred in the instant invention, more teeth get progressively involved in the cutting. As show in FIG. 6B, tooth contact is not progressive as in FIG. 5B.

Moreover, having thus described the invention, it should be apparent that numerous structural modifications and adaptations may be resorted to without departing from the scope and fair meaning of the instant invention as set forth hereinabove and as claimed hereinbelow.

We claim:

1. A surgical saw blade for use in combination with a surgical bone saw, the surgical saw blade comprising:

a) a proximal end configured to couple to a surgical bone saw;

b) a distal end having an even number of substantially identically teeth for cutting bone, each of the plurality of teeth ending in a tip distally; and c) a centrally positioned long axis between the proximal end and the distal end;

wherein each of the plurality of substantially identically shaped teeth are shaped substantially as right triangles including a hypotenuse and an angle opposite the hypotenuse, wherein each hypotenuse is oriented toward the centrally positioned long axis, and wherein the tips are arrayed on a line perpendicular to the centrally positioned long axis.

2. The surgical saw blade of claim 1 further comprising a centrally positioned tooth on the distal end, the centrally positioned tooth shaped substantially as an isosceles triangle.

3. The surgical saw blade of claim 1, wherein the even number of teeth are at least eight teeth.

4. The surgical saw blade of claim 1, wherein the angle opposite each hypotenuse is greater than 90°.

5. A method of cutting bone comprising the steps of:

a) providing a surgical saw blade according to claim 1;

b) coupling the saw blade to a surgical saw;

c) actuating the surgical saw with the coupled saw blade; and d) cutting a bone.

6. The method of claim 5 wherein the surgical saw blade provided in step a) further comprises a centrally positioned tooth on the distal end, the centrally positioned tooth shaped substantially as an isosceles triangle.

7. The method of claim 5, wherein the even number of teeth of the saw blade provided in step a) are at least eight teeth.

8. The combination of claim 5, wherein the angle opposite each hypotenuse of the plurality of teeth provided in step a) is greater than 90°.

9. In combination, a surgical bone saw and a bone saw comprising:

a) an oscillatory or sagittal bone saw; and b) a surgical saw blade having;

i) a proximal end configured to couple to a surgical bone saw;

ii) a distal end having an even number of substantially identically shaped teeth for cutting bone, each of the plurality of teeth ending in a tip distally; and iii) a centrally positioned long axis between the proximal end and the distal end;

wherein each of the plurality of teeth are substantially identically shaped substantially as right triangles including a hypotenuse and an angle opposite the hypotenuse, wherein each hypotenuse is oriented toward the centrally positioned long axis, and wherein the tips are arrayed on a line perpendicular to the centrally positioned long axis; and wherein the surgical saw blade is coupled to the oscillatory or sagittal bone saw.

10. The combination of claim 9 wherein the surgical saw blade further comprising a centrally positioned tooth on the distal end, the centrally positioned tooth shaped substantially as an isosceles triangle.

11. The combination of claim 9, wherein the even number of teeth of the saw blade are at least eight teeth.

12. The combination of claim 9, wherein the angle opposite each hypotenuse is greater than 90°.

* * * * *